United States Patent [19]

Chasar

[11] Patent Number: 4,520,151

[45] Date of Patent: May 28, 1985

[54] TRIS (3,6-DI-T-BUTYL-2-NAPHTHYL) PHOSPHITE AND COMPOSITIONS THEREOF

[75] Inventor: Dwight W. Chasar, Northfield, Ohio

[73] Assignee: The B. F. Goodrich Company, Akron, Ohio

[21] Appl. No.: 364,593

[22] Filed: Apr. 2, 1982

[51] Int. Cl.$^3$ .................. C08K 5/34; C08K 5/52; C07F 9/141

[52] U.S. Cl. .................. 524/101; 252/400 A; 260/967; 524/150

[58] Field of Search .................. 252/400 A; 260/967; 524/101, 150, 151

[56] References Cited

U.S. PATENT DOCUMENTS

| | | | |
|---|---|---|---|
| 2,058,343 | 10/1936 | Moran et al. | 524/151 |
| 2,419,354 | 4/1947 | Howland et al. | 524/151 |
| 2,572,571 | 10/1951 | Marling | 524/151 |
| 3,349,058 | 10/1967 | Mills et al. | 524/151 |
| 3,702,837 | 11/1972 | Gilles | 524/101 |
| 3,769,367 | 10/1973 | Factor | 524/151 |
| 4,187,212 | 2/1980 | Zinke et al. | 524/101 |

OTHER PUBLICATIONS

Fernand Chevassus et al.: The Stabilization of Polyvinyl Chloride, (1963), pp. 145–148.

*Primary Examiner*—Veronica P. Hoke
*Attorney, Agent, or Firm*—J. Hughes Powell, Jr.; Nestor W. Shust

[57] ABSTRACT

Tris (3,6-di-t-butyl-2-naphthyl) phosphite is a heat and hydrolysis resistant stabilizer for organic materials subject to heat and ultra-violet degradation, and in combination with hydroxy-phenylalkyleneyl isocyanurates, provides a useful synergistic combination for use in polymers, particularly hydrocarbon polymers including the poly(olefins).

12 Claims, No Drawings

TRIS (3,6-DI-T-BUTYL-2-NAPHTHYL) PHOSPHITE AND COMPOSITIONS THEREOF

BACKGROUND OF THE INVENTION

U.S. Pat. No. 2,572,571 discloses tris($\beta$-naphthyl)-phosphite as a stabilizer to prevent the discoloration of vinyl chloride polymers caused by heat. It has also been suggested as a stabilizer, with $\beta$-naphthol, for polyamides. However, tris($\beta$-naphthyl)phosphite has not been found to be satisfactory as a heat or U.V. stabilizer for hydrocarbon polymers, i.e., polymers of butadiene-1,3, isoprene and olefins such as poly(propylene) and (butylene). Tris($\beta$-naphthyl)phosphite is also subject to hydrolysis. A phosphite stabilizer that is more effective as a stabilizer for hydrocarbon and other polymers and is less susceptible to hydrolysis is desired.

SUMMARY OF THE INVENTION

Tris(3,6-di-t-butyl-2-naphthyl)phosphite is an effective stabilizer for materials subject to heat and UV degradation, and provides a synergistic combination that is particularly useful for stabilizing polymers when combined with a hydroxyphenylalkylenyl isocyanurate to provide polymer compositions having an excellent balance of oxidative/thermal and ultraviolet light stability.

DETAILED DESCRIPTION

The hydroxyphenylalkyleneyl isocyanurate compounds have the formula

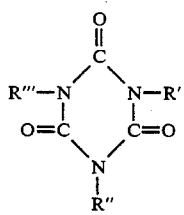

wherein R' is a hydroxyphenylalkyleneyl radical of the formula

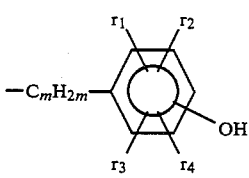

where m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms; and R'' and R''' are hydrogen, an alkyl radical containing 1 to 18 carbon atoms, or are the same as R'. A more preferred compound is when R'' and R''' are equal to R', i.e., all the R groups are hydroxyphenylalkyleneyl radicals, and $r_1$ is a t-alkyl radical containing from 4 to about 12 carbon atoms, $r_2$ is an alkyl radical containing 1 to about 12 carbon atoms, $r_3$ and $r_4$ are hydrogen, and m=1.

Even more preferred are the symmetrical tris(3,5-ditert-alkyl-4-hydroxybenzyl)isocyanurates of the formula

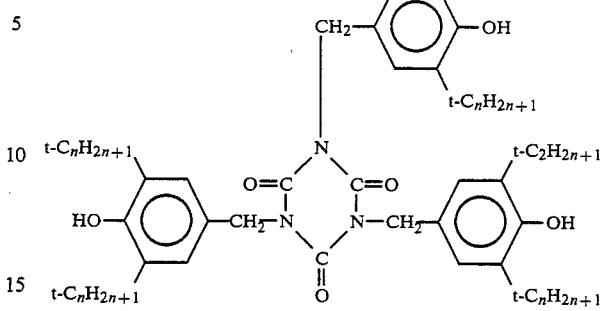

where n is 4 to 8.

Examples of the 4-hydroxybenzyl isocyanurate compounds are: tris-(3-t-butyl-4-hydroxybenzyl)isocyanurate, tris-(3-cetyl-4-hydroxybenzyl)-isocyanurate, tris(3,5-dimethyl-4-hydroxybenzyl)isocyanurate, tris-(3-methyl-5-isopropyl-4-hydroxybenzyl)isocyanurate, tris-(3,5-di-t-butyl-4-hydroxybenzyl)isocyanurate, tris-(3-t-butyl-5-t-amyl-4-hydroxy-benzyl)isocyanurate, tris-[3,5-di-(1-methyl-l-ethylpropyl)-4-hydroxybenzyl-]isocyanurate, tris-[3,5-di-(1,1,2,2-tetramethylpropyl)-4-hydroxybenzyl]isocyanurate, bis-[3,5-dimethyl-4-hydroxybenzyl)isocyanurate, (3-methyl-4-hydroxybenzyl)isocyanurate, (3-t-butyl-4-hydroxybenzyl)isocyanurate, and the like. Reference is made to U.S. Pat. No. 3,531,483 which discloses isocyanurate compounds encompassed by this invention. The patent is hereby incorporated by reference.

The amount of tris(3,6-di-t-butyl-2-naphthyl)phosphite used may vary from about 0.01 to 10 weight parts per 100 weight parts of material to be stabilized. More usually about 0.1 to 4.0 parts are used for mixtures with the hydroxyphenyl-alkyleneyl isocyanurate. The hydroxyphenylalkyleneyl isocyanurate compound is used at a level from about 0.01 part to about 5 parts by weight, and more preferably at from about 0.05 part to about 3 parts by weight per 100 parts by weight of the organic material. The phosphite compound is employed at similar levels, i.e., from about 0.01 part to 5 parts and preferably at about 0.05 part to about 3 parts by weight per 100 parts by weight of organic material. Thus the combined weight of the compounds is normally from about 0.02 part to about 10 parts and more preferably from about 0.1 to 6 parts by weight per 100 parts by weight of organic material. The hydroxyphenyl-alkyleneyl isocyanurate can be used in from about 10:1 to 1:10 weight ratio of isocyanurate compound to phosphite compound. Excellent results are obtained at about a 3:1 to 1:3 weight ratio. A 1:1 weight ratio of the compounds provides effective stabilization of organic materials.

Both the tris(3,6-di-t-butyl-2-naphthyl)phosphite and the combinations of the isocyanurate compound and the phosphite compound as defined herein provide exceptional heat and UV light stability to polyolefin polymers. The combination is especially useful for the stabilization of $\alpha$-monoolefin homopolymers and copolymers, wherein the $\alpha$-monoolefin contains 2 to about 8 carbon atoms. High and low-density polyethylene, isotactic and atactic polypropylene, polyisobutylene, and poly(4-methyl-l-pentene) have excellent resistance to UV light when stabilized with the combinations of the present invention. Ethylene-propylene (EP) copolymers and ethylene-propylene (EPDM) terpolymers generally containing less than about 10% by weight of one or more monomers containing multiple unsaturation also are stabilized using the combination.

Other organic materials which can be stabilized in accordance with the present invention include both natural and synthetic polymers. The stabilizers are useful for the stabilization of cellulosic materials; natural rubber, halogenated rubber, conjugated diene polymers, as, for instance, polybutadiene, copolymers of butadiene with styrene, acrylonitrile, acrylic acid alkyl acrylates or methacrylates, methyl vinyl ketone, vinyl pyridine, etc.; polyisoprene, polychloroprene, and the like; vinyl polymers such as polyvinyl chloride, polyvinylidene chloride, copolymers of vinyl chloride with vinylidene chloride, polyvinyl acetate, copolymers of vinyl halide with butadiene, styrene, vinyl esters, $\alpha,\beta$-unsaturated ketones and aldehydes, and the like; homopolymers and copolymers of acrylic monomers such as methyl acrylate, methyl methacrylate, ethyl acrylate, 3-ethylhexyl acrylate, acrylamide, methacrylamide, N-methylol-acrylamide, acrylonitrile, methacrylonitrile, and the like; polyether- or polyol-derived polyurethanes; acetal homo-polymers and copolymers; polycarbonates; polyesters such as those derived from maleic, fumaric, itaconic, or terephthalic anhydrides, or the like; for example, polyethylene terephthalate; polyamides such as those derived from the reaction of hexamethylenediamine with adipic or sebacic acid; epoxy resins such as those obtained from the condensation of epichlorohydrin with bisphenols; and the like. Polymer blends, that is, physical admixture of two or more polymers may also be stabilized in accordance with the present invention.

In addition to polymeric materials, the present compounds may stabilize a wide variety of other organic materials. Such compounds include: waxes, synthetic and petroleum-derived lubricating oils and greases; animal oils such as, for example, fat, tallow, lard, cod-liver oil, sperm oil; vegetable oils such as castor, linseed, peanut, palm, cotton seed, and the like; fuel oil; diesel oil, gasoline, and the like.

The compounds are readily incorporated into materials by dissolving or dispersing them within the materials. If the material is a solid, especially a polymeric solid such as a rubber or a plastic, the compounds can be admixed using Banburys, extruders, two-roll mills, and the like, following conventional techniques. One way to disperse the compounds in plastic materials is to dissolve or suspend the compounds in a solvent, mix the mixture with a plastic in powder form, and then evaporate the solvent.

Compositions containing the novel combination of compounds can also contain many other known compounding ingredients such as fillers like carbon black, silica, metal carbonates, talc, asbestos, and the like; pigments and colorants; curative ingredients like sulfur and peroxides and vulcanization accelerators; fungicides and many more standard ingredients known to the art. As the combination is particularly useful as a ultra-violet light stabilizer, other ingredients known in the art as ultra-violet light, thermal, and/or oxidative stabilizers can also be used in the UV light stabilized compositions.

Samples were prepared by mixing the stabilizer compounds with polypropylene in a Brabender Plasticorder fitted with a Cam-Head (mixing chamber). The polypropylene is first masticated for 1½ minutes at 190° C. Then the stabilizer mixture is added, followed by 3 minutes additional mixing. The mass is removed and pressed into 20 mil thick sheets. From these sheets are cut 1"×1" plaques for oven-aging. Type C (3"×⅛") tensil bars are cut for UV stability tests.

Thermal/oxidative stability (oven aging) testing consisted of aging the samples in triplicate in an air-circulating oven at 125° C. The time to catastrophic crumbling (failure) of the plaque is measured.

The UV stability of the compositions was evaluated as follows. Tensile bars are clamped on a frame and placed in an Atlas Xenon Weatherometer Model No. 65-WR equipped with a 6500 watt Xenon burner tube. The black panel temperature is 60° C. The samples are subjected to an 18 minute water cycle every two hours.

The following examples demonstrate the practice of the invention in specific embodiments.

EXAMPLE 1

Tris(3,6-di-t-butyl-2-naphthyl)phosphite is prepared by adding 20 grams (0.078 mole) of 3,6-di-t-butyl $\beta$-naphthol, 8 grams of triethylamine (0.079 mole) and 100 ml. of toluene to a reactor equipped with thermometer, condensor, dropping funnel, and a nitrogen inlet. 3.6 grams of $PCl_3$ (0.026 mole) was dissolved in 20 ml. of toluene. After flushing the reactor with nitrogen, the $PCl_3$ solution was added dropwise to the reactor with stirring at room temperature. All of the $PCl_3$ solution was added over a 10 minute period, the reaction was stopped after 3 hours, and was worked up by first filtering the reaction mixture, washing twice with water, and drying over $MgSO_4$ and under vacuum. The product was then washed twice with methanol to provide a white solid. This material has a melting point of 226°–236° C. The structure was identified and confirmed by Infra-Red, Nuclear Magnetic Resonance, Mass Spectrometery and elemental analysis. This phosphite is a very stable compound even at 350° C. and is not susceptible to hydrolysis as compared to tris $\beta$-naphthyl)phosphite.

EXAMPLE 2

In this example, the effect of heat aging and Weatherometer exposure is shown for tris(3,6-di-t-butyl-2-naphthyl)phosphite as compared to the prior art tris($\beta$-naphthyl)phosphite. 20 mil polypropylene plaques containing 0.1 weight part of phosphite per hundred weight parts (phr) of polypropylene were prepared by the aforedescribed procedures. Samples were tested for heat aging in an oven at 125° C. until failure, as shown by catastrophic crumbling or embrittlement of the plaque. The tris($\beta$-naphthyl)phosphite sample failed after 8⅔ days while the tris(3,6-di-t-butyl-2-naphthyl)-phosphite sample did not fail until after 11⅘ days. In the Weatherometer, (ASTM# D2565-79-A) demonstrating resistance to ultra-violet light degradation, the time to a 50% loss in tensile strength was measured. For the tris-($\beta$-naphthyl)phosphite, the samples lost 50% tensile strength after 160 hours, while samples containing the tris(3,6-di-t-butyl-2-naphthyl)phosphite did not lose 50% tensile strength until after 380 hours.

EXAMPLE 3

This example sets forth the unexpected synergistic effect obtained with the tris(3,6-di-t-butyl-2-naphthyl)-phosphite and a hydroxyphenylalkylene isocyanurate, 1,3,5-tris(3,5-di-t-butyl-4-hydroxybenzyl)isocyanurate.

Three polypropylene samples were made up as 20 mil. plaques containing (1) 0.1 phr of 1,3,5-tris(3,5-di-t-butyl-4-hydroxybenzyl)isocyanurate, (2) 0.1 phr of tris(3,6-di-t-butyl-2-naphthyl)phosphite and (3) 0.05 phr each of (1) and (2). At 125° C. (1) failed after $43\frac{2}{3}$ days, (2) failed after $9\frac{1}{3}$ days, and (3), the synergistic combination, did not fail until $95\frac{1}{3}$ days.

EXAMPLE 4

This example demonstrates the effect of water on the heat stabilizing efficiency of tris($\beta$-naphtyl)phosphite and tris(3,6-di-t-butyl-2-naphthyl)phosphite in polypropylene. 10 mil polypropylene plaques were prepared containing 0.1 phr each of the two phosphites. The samples were soaked in distilled water for 72 hours, drained and then oven aged at 125° C. until failure. The sample containing the tris-($\beta$-naphthyl)phosphite failed after $5\frac{1}{3}$ days. The sample containing the tris(3,6-di-t-butyl-2-naphthyl)phosphite did not fail until after $7\frac{1}{3}$ days, thus demonstrating its better resistance to hydrolysis.

I claim:

1. Tris(3,6-di-t-butyl-2-naphthyl)phosphite.

2. A composition comprising organic materials subject to degradation and a stabilizing amount of tris(3,6-di-t-butyl-2-naphthyl)phosphite.

3. A composition of claim 2 wherein the organic material is a polyolefin polymer.

4. A stabilizer for polyolefin materials subject to degradation comprising (1) a hydroxyphenylalkyleneyl isocyanurate of the formula

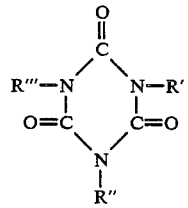

wherein R' is a hydroxyphenylalkyleneyl radical of the formula

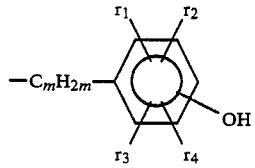

where m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms, and R'' and R''' are hydrogen, an alkyl radical containing 1 to 18 carbon atoms, or are the same as R', and (2) tris(3,6-di-t-butyl-2-naphthyl)phosphite.

5. A stabilizer of claim 4 wherein in (1) R'' and R''' are equal to R', $r_1$ is a tertiary alkyl radical containing 4 to about 12 carbon atoms, $r_2$ is an alkyl radical containing 1 to about 12 carbon atoms, $r_3$ and $r_4$ are hydrogen, and m=1.

6. Stabilizer of claim 5 where (1) has the formula

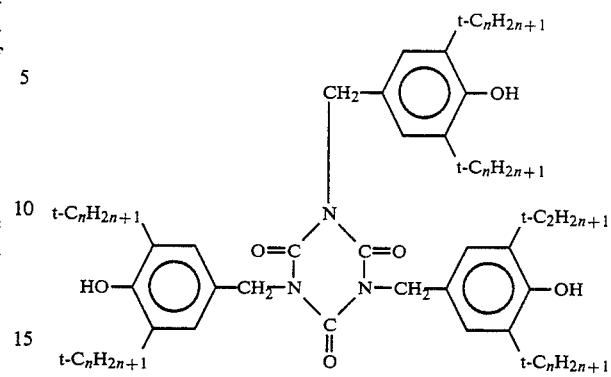

where n is 4 to 8.

7. The stabilizer of claim 6 where (1) is 1,3,5-tris(3,5,-di-t-butyl-4-hydroxybenzyl)isocyanurate.

8. A composition comprising a polyolefin polymer, (1) a hydroxyphenylalkyleneyl isocyanurate of the formula

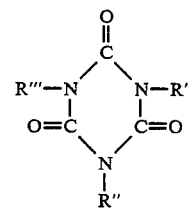

wherein R' is a hydroxyphenylalkyleneyl radical of the formula

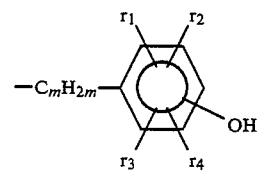

where m is 1 to 4, $r_1$ is an alkyl radical having 1 to 18 carbon atoms and is positioned immediately adjacent to the hydroxyl group on the ring; $r_2$, $r_3$, and $r_4$ are hydrogen or an alkyl radical containing to 18 carbon atoms; and R'' and R''' are hydrogen, an alkyl radical containing 1 to 18 carbon atoms, or are the same as R', and (2) tris(3,6-di-t-butyl-2-naphthyl)phosphite.

9. A composition of claim 8 wherein said polymer is a polymonoolefin polymer, and in (1), R'' and R''' are the same as R', $r_1$ is a tertiary alkyl radical containing 4 to about 12 carbon atoms, $r_2$ is an alkyl radical containing 1 to about 12 carbon atoms, $r_3$ and $r_4$ are hydrogen, and m=1.

10. A composition of claim 9 wherein said polymer is polypropylene.

11. A composition of claim 10 where in (1) has the formula

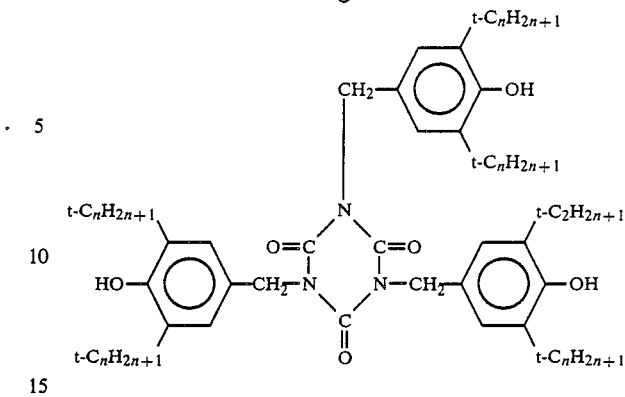
where n is 4 to 8.
12. A composition of claim 11 where (1) is 1,3,5-tris(3,5-di-t-butyl-4-hydroxybenzyl)isocyanurate.
* * * * *

UNITED STATES PATENT AND TRADEMARK OFFICE
CERTIFICATE OF CORRECTION

PATENT NO. : 4,520,151
DATED : May 28, 1985
INVENTOR(S) : DWIGHT WILLIAM CHASAR

It is certified that error appears in the above-identified patent and that said Letters Patent is hereby corrected as shown below:

The formula in Claim 6, line 10 should read as follows:

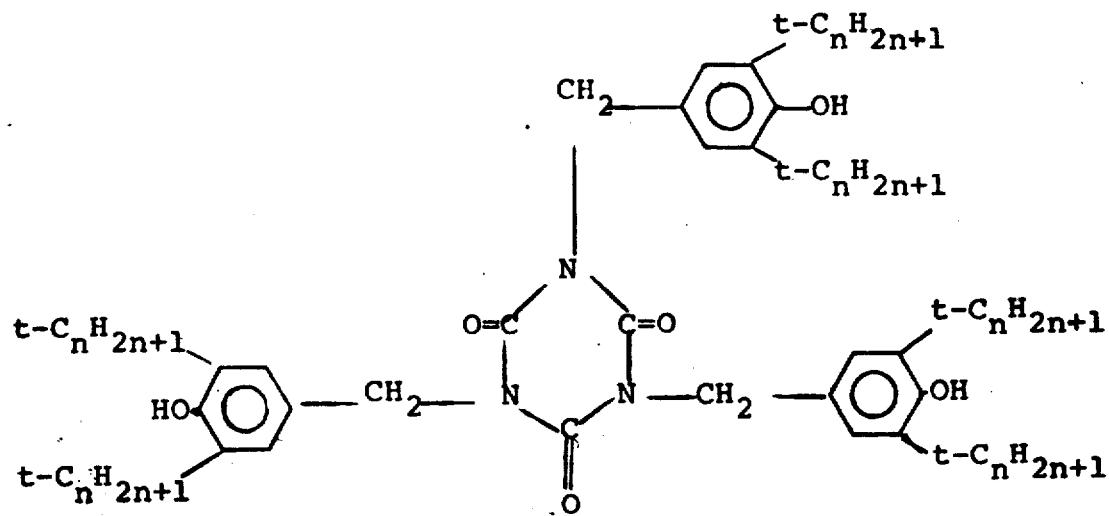

Signed and Sealed this

Twentieth Day of May 1986

[SEAL]

Attest:

DONALD J. QUIGG

Attesting Officer   Commissioner of Patents and Trademarks

UNITED STATES PATENT AND TRADEMARK OFFICE
CERTIFICATE OF CORRECTION

PATENT NO. : 4,520,151
DATED : May 28, 1985
INVENTOR(S) : DWIGHT WILLIAM CHASAR

It is certified that error appears in the above-identified patent and that said Letters Patent are hereby corrected as shown below:

Claim 11, column 8, line 9 " $t\text{-}C_2H_{2n+1}$ "

should read -- $t\text{-}C_nH_{2n+1}$ --

Signed and Sealed this

Twelfth Day of August 1986

[SEAL]

Attest:

DONALD J. QUIGG

*Attesting Officer*  *Commissioner of Patents and Trademarks*